(12) United States Patent
Whitmore, III et al.

(10) Patent No.: US 8,401,617 B2
(45) Date of Patent: Mar. 19, 2013

(54) EM TRACKING SYSTEMS FOR USE WITH ULTRASOUND AND OTHER IMAGING MODALITIES

(75) Inventors: Willet F. Whitmore, III, Longboat Key, FL (US); Craig J. Cermak, Riverside, IA (US)

(73) Assignee: CIVCO Medical Instruments Co., Inc., Kalona, IA (US)

(*) Notice: Subject to any disclaimer, the term of this patent is extended or adjusted under 35 U.S.C. 154(b) by 0 days.

(21) Appl. No.: 13/305,266

(22) Filed: Nov. 28, 2011

(65) Prior Publication Data

US 2012/0071754 A1 Mar. 22, 2012

Related U.S. Application Data

(62) Division of application No. 12/335,061, filed on Dec. 15, 2008, now Pat. No. 8,086,298.

(60) Provisional application No. 61/100,870, filed on Sep. 29, 2008.

(51) Int. Cl.
*A61B 5/05* (2006.01)
*A61B 8/14* (2006.01)

(52) U.S. Cl. .................................. 600/424; 600/459

(58) Field of Classification Search .............. 600/407, 600/424, 585, 114, 117, 121; 128/899
See application file for complete search history.

(56) References Cited

U.S. PATENT DOCUMENTS

| 5,676,673 | A | 10/1997 | Ferre et al. |
|---|---|---|---|
| 6,332,891 | B1 | 12/2001 | Himes |
| 6,572,593 | B1 | 6/2003 | Daum |
| 6,783,536 | B2 | 8/2004 | Vilsmeier et al. |
| 7,366,562 | B2 | 4/2008 | Dukesherer et al. |
| 7,840,251 | B2 | 11/2010 | Glossop |
| 7,926,776 | B2 | 4/2011 | Cermak |
| 2005/0090742 | A1 | 4/2005 | Mine et al. |
| 2007/0232882 | A1 | 10/2007 | Glossop et al. |
| 2008/0218743 | A1 | 9/2008 | Stetten et al. |
| 2009/0275833 | A1* | 11/2009 | Ikeda et al. .................. 600/443 |

FOREIGN PATENT DOCUMENTS

| EP | 1932477 A1 | 6/2008 |
|---|---|---|
| WO | 2004019799 A2 | 3/2004 |
| WO | 2006074509 A1 | 7/2006 |

OTHER PUBLICATIONS

International Search Report for Application No. PCT/US2009/058075 dated Feb. 8, 2010.

* cited by examiner

*Primary Examiner* — Michael Rozanski
(74) *Attorney, Agent, or Firm* — Caesar, Rivise, Bernstein, Cohen & Pokotilow, Ltd.

(57) ABSTRACT

An EMT system for use in ultrasound and other imaging modality guided medical procedures. The system includes a tool set of various components to which EM sensors can be releasably secured. Thus, the sensors can be reused, notwithstanding the disposal of other components of the tool set. Various components of the tool set include keying elements to facilitate their registration to the anatomy of the patient undergoing the procedure via the EM sensors.

23 Claims, 10 Drawing Sheets

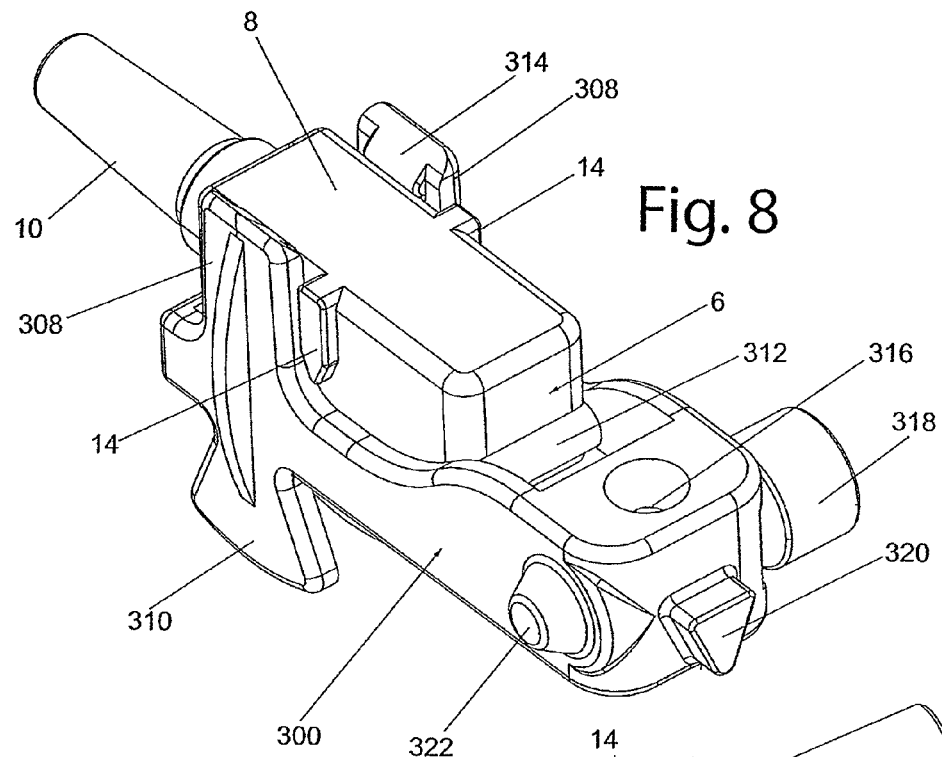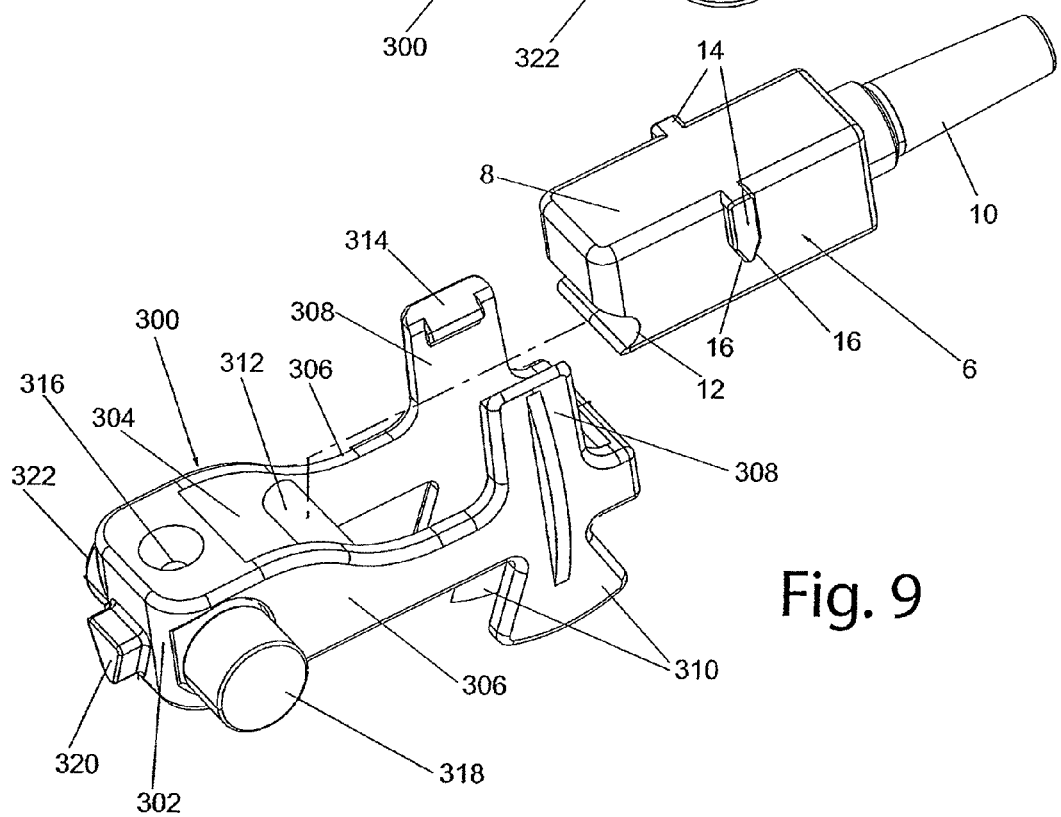

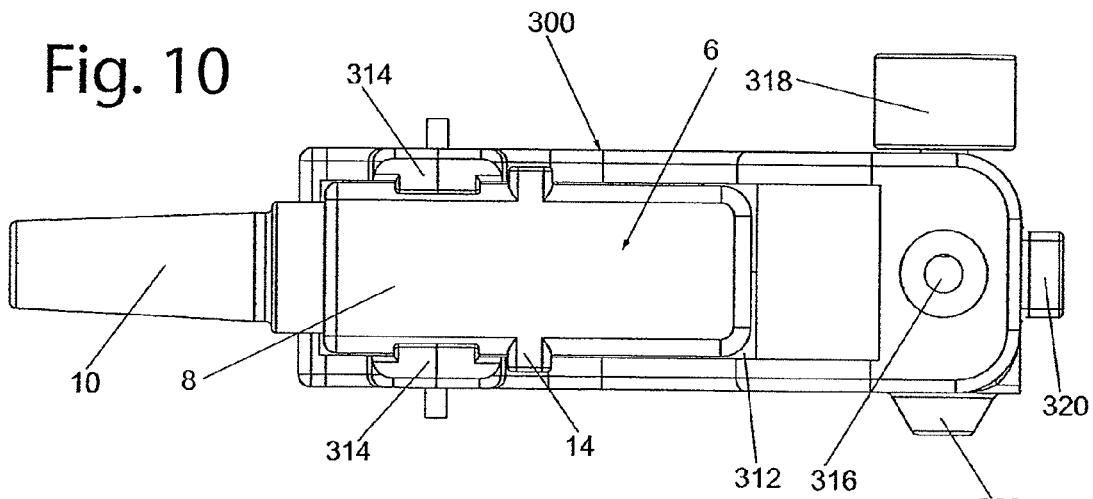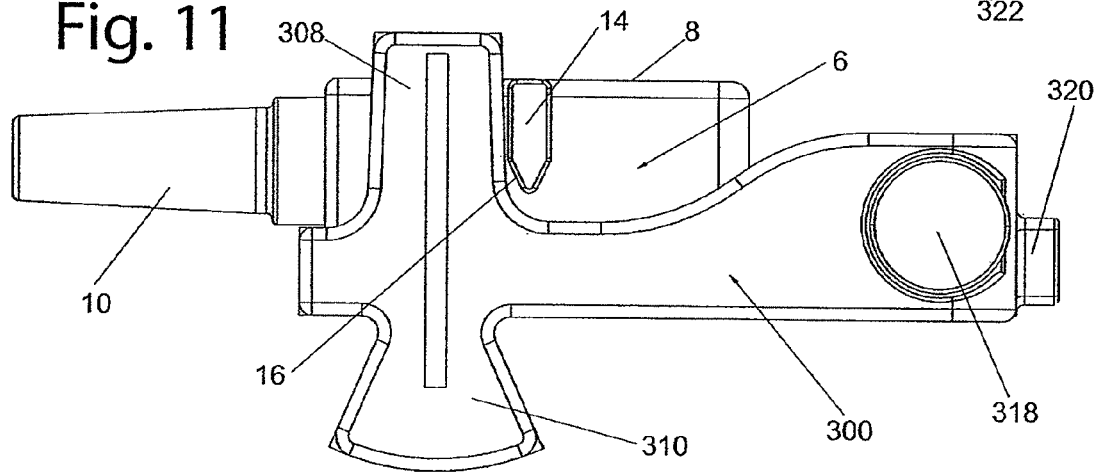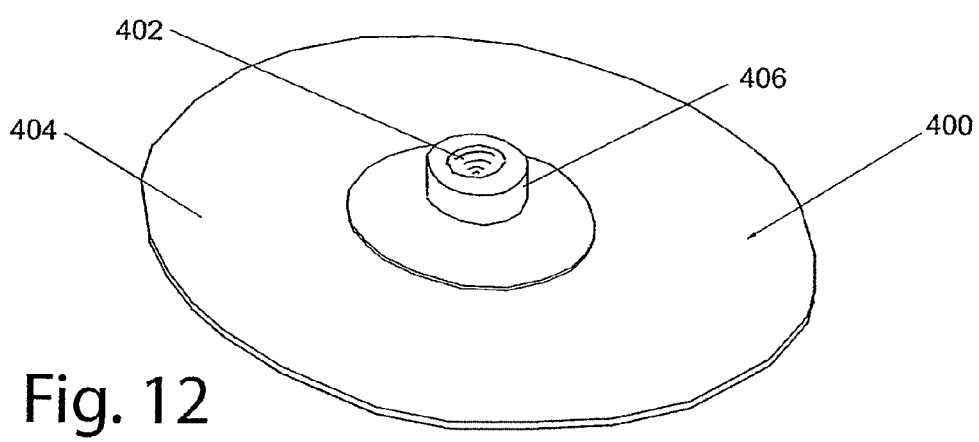

EM TRACKING SYSTEMS FOR USE WITH ULTRASOUND AND OTHER IMAGING MODALITIES

CROSS-REFERENCE TO RELATED APPLICATIONS

This divisional application claims the benefit under 35 U.S.C. §121 of application Ser. No. 12/335,061, filed on Dec. 15, 2008, now U.S. Pat. No. 8,086,298, which in turn claims the benefit under 35 U.S.C. §119(e) of Provisional Patent Application Number 61/100,870, filed on Sep. 29, 2008, the contents all of which are incorporated herein by reference.

STATEMENT REGARDING FEDERALLY SPONSORED RESEARCH OR DEVELOPMENT

"Not Applicable"

INCORPORATION-BY-REFERENCE OF MATERIAL SUBMITTED ON A COMPACT DISK

"Not Applicable"

FIELD OF THE INVENTION

This invention relates generally to medical instrument tracking system and more particularly to tools sets enabling the use of electromagnetic (EM) field multidimensional tracking technology for instrument guidance within a patient using medical images (both 2-D and 3-D data sets of real time and/or delayed and/or fused images) registered to a patient.

BACKGROUND OF THE INVENTION

Ultrasound has received widespread acceptance as a useful diagnostic tool by providing an image of the internal area of inquiry by emission of very high frequency sound waves from a transducer (commonly called a "probe") placed in contact with the patient's skin adjacent that area of inquiry. Repeated arrays of ultrasonic beams scan that area and are reflected back to the transducer, where the beams are received and the data transmitted to a processing unit. A processing unit, to which the probe is connected, analyzes the information and composes a picture for display on an associated monitor screen. For some applications the determination of the precise position or location of the probe in real time with respect to the patient's body is desirable, e.g., to correlate, register or "fuse" the ultrasonic image to other scans (digital image sets), such as CT scans, MR scans, PET scans, and the like. This real time correlation matched with targeting software can be combined with real time tracking and navigation systems and devices to navigate an instrument within a patient for minimally invasive procedures. In other settings such as CT, when ultrasound is not available or useful virtual navigation of an instrument within a patient also may be image-guided by having the images registered to the patient using fiducial markers and also registered to a navigation and tracking device or system using recently acquired volume images (data sets) that are then co-registered to both the images and the navigation system.

Optical and electromagnetic tracking (EMT) technologies are two non-mechanical, real-time, approaches for accurate instrument tracking and navigation using appropriately registered volume images (digital data sets). Both optical and electromagnetic technologies have advantages and limitations, but on balance the technological advantages of EMT for minimally invasive procedures are dominant. In particular, EMT is believed to be the preferable technology because of the ability to track objects inside the body (beyond line-of sight) and the compact size of the tracked sensors. These powered sensors typically provide position and orientation data sets of 5 or 6 degrees-of-freedom (DOF) and combined with the electronic cables required are relatively expensive.

EMT systems that support image fusion and instrument tracking are commercially available and disclosed in the patent literature. They typically enable determination of 5 or 6 DOF orientation and position of an instrument, such as a needle, by determining location, orientation, and/or positioning information relative to some coordinate system. For example, Ascension Technology Corporation makes 5 and 6 DOF position and orientation tracking devices suitable for various medical applications, e.g., to navigate, localize, and guide medical instruments for image-guided procedures. Other manufacturers/suppliers of EM tracking systems include Polhemus, Inc. Northern Digital Inc. and Medtronic, Inc. Suppliers of software, tracked needles and other instruments for clinical use that utilize these technologies in medical procedures include Traxtal Corporation and Veran Medical. Image fusion in combination with ultrasound is available from Traxtal, Inc., GE Healthcare Ultrasound and Esaote Ultrasound, among others.

Typically these tracking systems use the attenuation of oriented electromagnetic signals to determine the absolute position and orientation of a sensor, relative to a source, e.g., a magnetic field generator. The source and the sensor are connected via cables to an electronics module, which contains a microcomputer and associated electronics of the system. The source typically includes three orthogonal coils that are pulsed in rotation, one after another. Each pulse transmits a radio frequency electromagnetic signal that is detected by the sensor. The sensor also contains two or three orthogonal coils, which measure the strength of the signal from the current source coil. By using the known pulse strength at the source and the known attenuation of the strength with distance, the position and orientation of the sensor coils can be calculated by the system via triangulation techniques.

Utilizing EM sensors with ultrasonic probes can be accomplished by permanently mounting the sensor(s) on the probe or by building such sensor(s) into the probe. However, the permanent mounting approach may not be desirable if the probe is also intended to be used in applications wherein its position need not be determined. Also, the inclusion of such sensor(s) permanently on or in the probe will likely increase the cost, complexity and service requirement of the probe. Therefore external attachment, when needed, has become the commercially dominant approach. The challenge in this case is to locate and attach, when required, the removable sensor (s) to the probe in a way that that is quick, secure and ergonomic. Thus, the use of some releasable mounting system has become a required element for registration and fusion of volume image data sets from CT, MR, PET, etc. for use during real time ultrasound imaging. This has been done by several companies to date, including GE Healthcare Ultrasound, Hitachi and Esaote Ultrasound.

In U.S. patent application Ser. No. 12/111,387, filed on Apr. 29, 2008, entitled "Bracket for Mounting At Least One Position Detecting Sensor On An Ultrasonic Probe", which is assigned to the same assignee as this invention and whose disclosure is incorporated by reference herein, there is disclosed a bracket for use with an ultrasound transducer to releasably mount at least one sensor of a location/tracking system on the transducer and serves as one unique solution to fulfill this commercial ideal.

Other medical components or devices making use of EM sensors have been provided as part of an EMT system for use with EM tracked ultrasound transducers and also may be used in properly registered CT or CT fused with PET or MR image sets without ultrasound. These devices include needles of all types, fiducial markers with EMT sensors embedded to aid with patient and image data registration, and other tracked devices. These tracked devices, especially the needles with sensors in the tip, have been shown to have great advantages for simplifying the safe and accurate placement of these instruments during minimally invasive procedures. However, to date most devices and all existing needles using EM tip sensors have the sensor(s) permanently attached and must be discarded after a single use or require time and expense to re-process and re-sterilize. In most cases the cost of these disposable devices makes the routine use of EM tracking and navigation cost-prohibitive. Thus, until now, expense has been a serious limiting factor to general adoption of EM technology for image guidance.

The subject invention entails a complete mechanical tool set that will allow re-use of all the expensive sensor components of an EMT system to greatly reduce costs per procedure in the rapidly expanding market for image fusion and guidance. While re-using the expensive 5 and 6 DOF powered (active) EM sensors will require a more complex setup and assembly process for each use, the payoff in reduced cost per procedure is believed to be so critical that the small extra time required for such set-up will be gladly tolerated.

The complete EMT tool set for providing image guidance in ultrasound applications and for other imaging modalities includes not only the subject matter of this invention (which will be described shortly), but also dedicated system software. It is anticipated that most of such registration, navigation and image fusion software will be developed and supplied by the original equipment manufacturers of the imaging hardware.

The system of this invention is in the form of an image fusion and navigation tool set that includes a number of components. Foremost among those components is a specially designed needle (trochar) with a reusable EM sensor in the tip of the stylet. Other components include, a specially designed ultrasound bracket to accept one or more reusable EM sensor(s) and a needle guide (e.g., a slotted needle guide enabling mechanical positioning of the linear instrument within the image plane of the ultrasound transducer). In addition, the subject tool set includes a releasably securable adapter device for mounting a reusable EM sensor on any needle or elongated medical instrument (e.g., biopsy needles, syringes, ablation needles, (cryoprobes, RF probes, catheters containing a stylet, etc.)) to convert that instrument into an EM trackable instrument (which will be accurate in the absence of bending/deflection beyond the attachment point of the device), and skin surface markers for facilitating three dimensional image registration and image fusion in certain circumstances (e.g., these may not be useful in cases where ultrasound is used because more accurate registration may be achieved using internal anatomic landmarks visible on real time images). Those markers can be either the passive or active types. Passive type markers are typically sterile adhesive devices that contain only a radio-opaque marker and/or a marker visible on MR imaging. The passive markers of this invention also include a keying feature for registration using an EM sensor (contained within a housing). Active type skin surface markers are typically non-sterile adhesive devices with embedded or attached EM sensors that can with proper software support provide continuous real-time automatic registration updates for image fusion and navigation. Traxtal, Inc. and Veran Medical Technologies provide skin surface markers with embedded EM sensors, while the present invention proposes skin surface markers with attachable EM sensors. In accordance with one aspect of the present invention in order to provide active markers, passive markers are supplemented with a mounting bracket that is adapted to receive a reusable EM sensor. In addition to the foregoing, it is anticipated that the EMT tool set will also include custom sterile disposable cover/drape packages to allow sterility and re-use without reprocessing of the expensive EM sensors and connecting cables.

The EMT tool set of the subject invention is intended to support any EM technology. and function with all imaging modalities alone or in combination (fusion). In particular, the components of the subject invention will enable CT, PET-CT, or MR image fusion with or without a real-time ultrasound image and 5 or 6 DOF navigation within the EM field. Properly applied, the technology of this invention will allow better visualization of target lesions in the body and highly accurate instrument navigation to reach them more quickly and safely. In particular, it is anticipated that the subject invention will be used by the full spectrum of clinicians that employ image guidance for reaching internal targets within a patient.

The subject invention's image fusion and navigation tool set is designed with a universal approach allowing components to be used across all OEM imaging platforms. It is anticipated that the subject invention will be utilized by physicians in the following specialties: interventional radiology, radiology, surgery and cardiology. Anticipated clinical applications are biopsy procedures, ablation procedures, catheter placements, intravascular procedures and endoscopic procedures.

All references cited and/or identified herein are specifically incorporated by reference herein.

SUMMARY OF THE INVENTION

In accordance with one aspect of the invention there is provided an instrument, e.g., a trochar, for insertion into the body of a patient via a sheath for use in an ultrasound-guided procedure on the patient, with the position of the instrument to be tracked with respect to the being by an EMT system. The instrument comprises an EM sensor and a first member. The first member comprises a first handle and an elongated linear stylet secured to and projecting from the first handle. The linear stylet has a distal tip portion and a hollow interior cavity terminating adjacent the distal tip portion. The EM sensor has an electrical cable connected to it. The EM sensor is disposed within the cavity located adjacent the distal tip portion of the stylet and with the electrical cable extending along the length of and out of the cavity. The sensor and the associated cable are arranged to be removed from the cavity of the stylet for reuse.

In accordance with another aspect of this invention there is provided a device for releasable mounting on an elongated, linear medical instrument used in an ultrasound-guided procedure on a patient, with the procedure being carried out by an ultrasound transducer to enable the position of the instrument to be tracked with respect to a patient by an EMT system. The instrument has a distal end portion. The device basically comprises an EM sensor and a housing for the sensor. The housing mounts the sensor and is releasably securable to the instrument at various positions along the length of the instrument. The housing comprises a first keying member arranged to be releasably coupled to the ultrasound transducer, e.g., to a slotted needle guide mounted on a bracket that is mounted on the ultrasound transducer, to enable the EMT system to register the sensor with respect to the ultrasound transducer. A second keying member may be provided on the ultrasound transducer, e.g., on the needle guide, so that the distal end portion of the instrument can be releasably coupled to the second keying member to enable the EMT system to register the distal end portion of the instrument with respect to the sensor.

In accordance with another aspect of this invention there is provided an instrument guide and/or a bracket for use on an ultrasound transducer in an ultrasound-guided procedure on a patient by an elongated linear instrument. The instrument has a distal end portion. The instrument guide and/or a bracket forms a portion an EMT system and is arranged to receive the instrument. The EMT system comprises a sensor including a housing having a first keying member. The instrument guide and/or a bracket includes a first keying member adapted to be releasably coupled to the first keying member of the sensor to enable the EMT system to register the sensor with respect to the ultrasound transducer. A second keying member may be provided on the instrument guide and/or a bracket so that the distal end portion of the instrument can be releasably coupled to the second keying member to enable the EMT system to register the distal end portion of the instrument with respect to the sensor.

In accordance with another aspect of this invention there is provided an EMT system for use in an ultrasound-guided procedure on a patient by an elongated linear instrument comprising a first component adapted for mounting on an ultrasound transducer and a second component including an EM sensor. The instrument has a distal end portion. The first component is arranged to receive the instrument. The second component comprises a sensor, including a housing for the sensor. The housing comprises a first keying member. The first component comprises a first keying member adapted to cooperate with the first keying member of the housing of the second component to enable the EMT system to register the sensor with respect to the ultrasound transducer. The first component may additionally comprises a second keying member so that the distal end portion of the instrument can be releasably coupled to the second keying member to enable the EMT system to register the distal end portion of the instrument with respect to the sensor.

In accordance with another aspect of this invention there is provided an EMT system for use in an ultrasound-guided procedure on a patient comprising a first component and a second component. The first component is a marker adapted for securement to the patient. The second component comprises a sensor including a housing for the sensor. The housing comprises a first keying member. The marker comprises a first keying member adapted to cooperate with the first keying member of the housing of the second component to enable the registration of the marker with respect to the body of a patient.

DESCRIPTION OF THE DRAWING

FIG. 8 is an enlarged isometric view of the instrument adapter shown in FIGS. 6 and 7 having an EM sensor mounted thereon, whereupon the sensor-equipped adapter can be used with any conventional medical needle or other elongated linear medical instrument (not shown) to convert the needle/instrument into an EM trackable needle/instrument;

FIG. 9 is an exploded isometric view of the sensor-equipped adapter of FIG. 8;

FIG. 10 is an enlarged top plan view of the sensor-equipped adapter of FIG. 8;

FIG. 11 is an enlarged side elevation view of one side of the sensor-equipped adapter of FIG. 8;

FIG. 12 is an isometric view of a passive EM marker constructed in accordance with this invention and having a keying feature constructed in accordance with another aspect this invention to enable a sensor-equipped adapter, like shown in FIG. 8, or some other sensor-equipped component to be used to register the marker in the EMT system of this invention;

DETAILED DESCRIPTION OF THE PREFERRED EMBODIMENT

Figure 1:
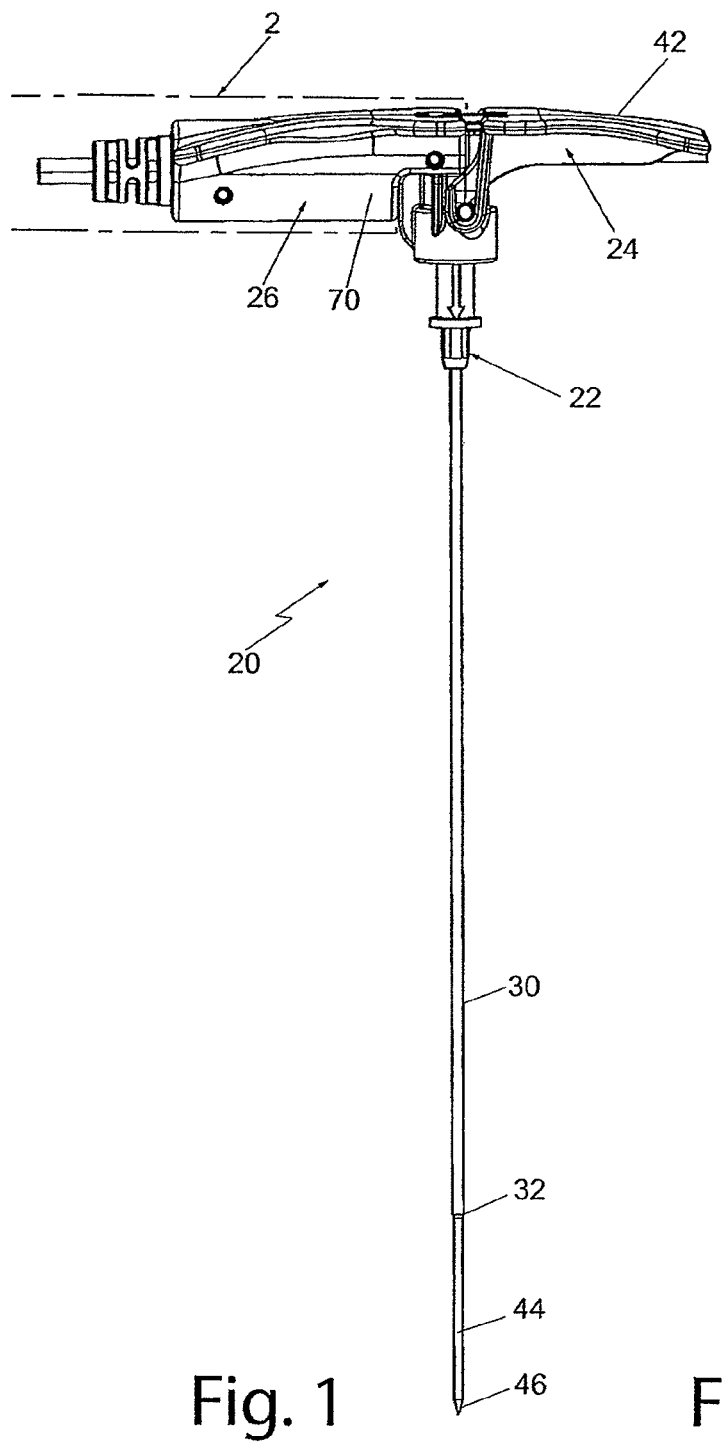
FIG. 1 is a side elevation view of an EM trackable trochar constructed in accordance with one aspect of this invention and forming a portion of the EMT system of this invention.

Referring now to the various figures of the drawing wherein like reference characters refer to like parts, there is shown in FIGS. 1-5B an EM trackable trochar 20 forming one portion of an EMT system tool set constructed in accordance with this invention. The EM tracking tool set also includes several other components, such as an EM sensor-equipped bracket 100 (shown in FIGS. 6-7), a slotted needle guide 200 (also shown in FIGS. 6-7), an EM sensor-equipped adapter 300 (shown in FIGS. 8-10), and an external skin marker 400 (shown in FIG. 12).

The details of each of the components of the tool set of this invention will be described later. Suffice it for now to state that the EM trackable trochar 20 includes an EM sensor and associated components which can be reused, while the other components of that device are designed for single use and then disposal.

The bracket 100 is arranged to be mounted on a conventional ultrasonic transducer 2, with a sterile cover (not shown) interposed therebetween and includes a mount for an EM sensor to enable the ultrasonic transducer to be registered to the anatomy of the patient undergoing the ultrasound procedure by the EMT system of which the sensor is a component.

The slotted needle guide 200 is arranged to be releasably mounted on the bracket 100 and includes a slot into which a needle, e.g., a conventional biopsy needle, can be inserted and its position detected and tracked by the ultrasonic transducer.

Figure 13:
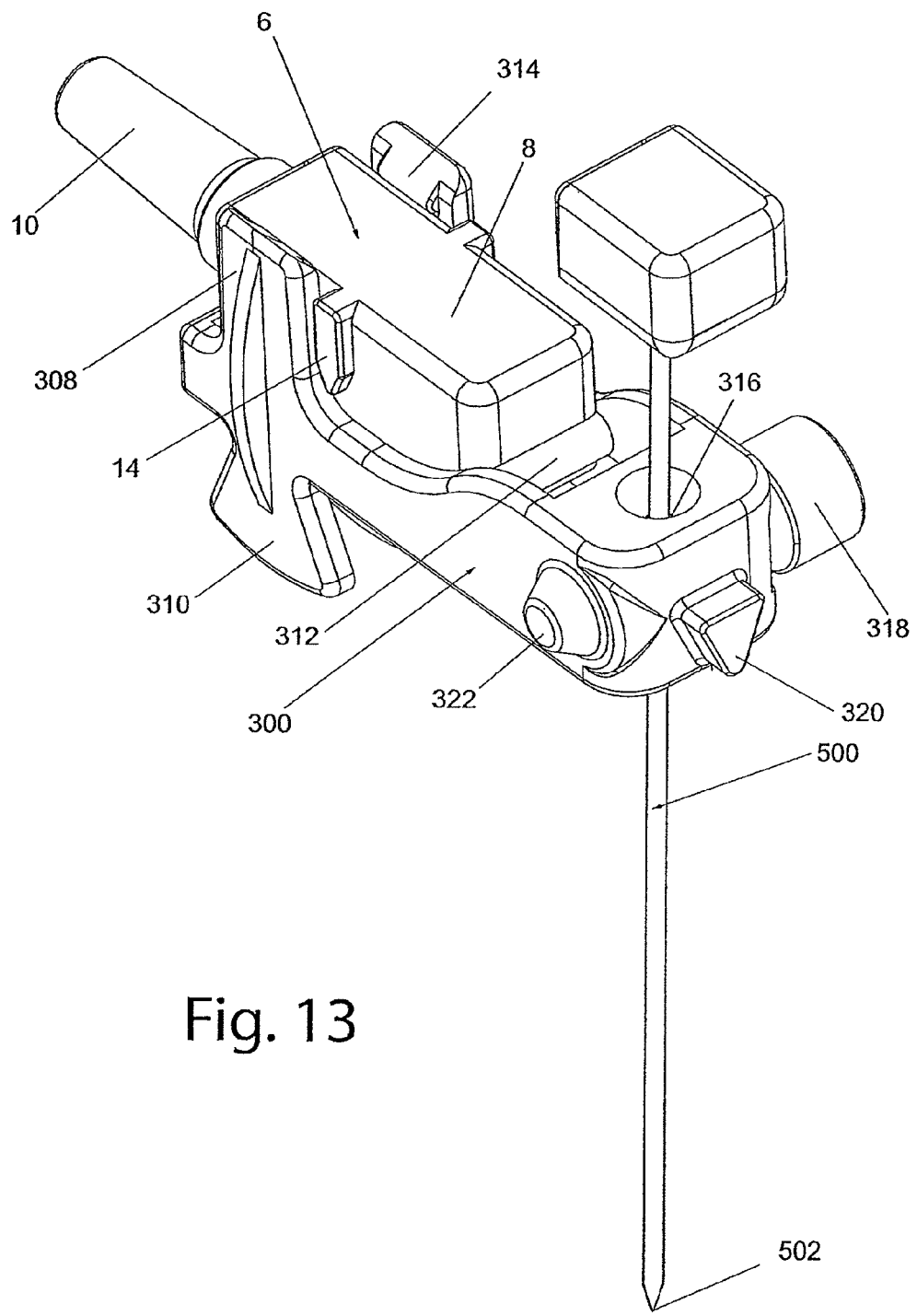
FIG. 13 is an enlarged isometric view showing the sensor-equipped adapter of FIG. 8 mounted on a conventional disposable needle to convert that needle into an EM trackable needle.
Figure 14:
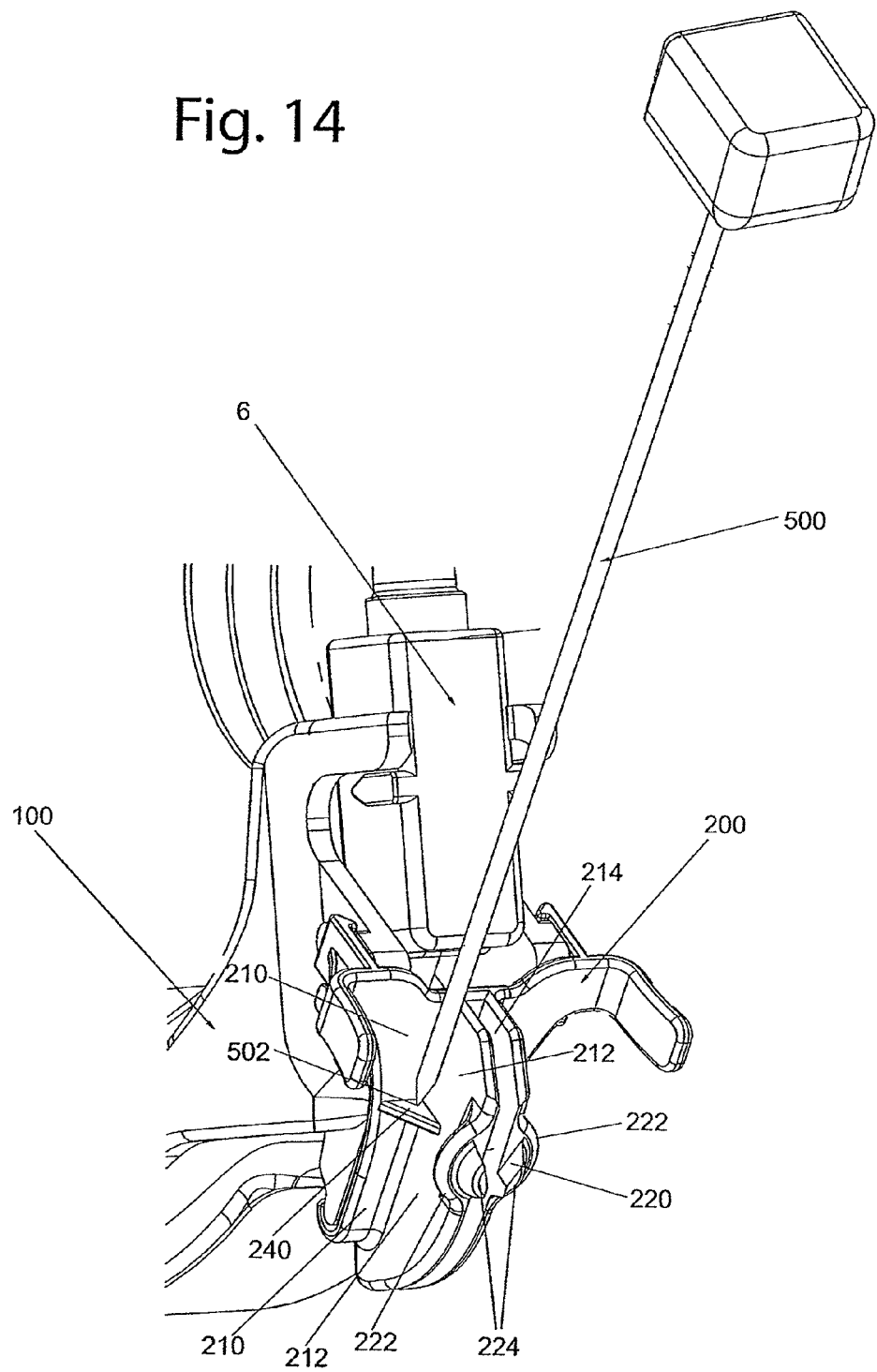
FIG. 14 is an enlarged isometric view showing the needle of FIG. 13 with the sensor-equipped adapter mounted thereon in the process of being registered to the ultrasonic transducer by the EMT system of this invention.

The EM sensor-equipped adapter 200 (shown in FIGS. 8-10) is arranged to be mounted on any conventional needle, such as shown in FIGS. 13 and 14, or any other elongated linear medical instrument to convert that needle/instrument into an EM trackable needle/instrument.

The external skin marker 300 is a device that is arranged to be releasably secured (e.g., by a releasable adhesive) to the skin of the patient to serve as a reference point for the EM tracking system.

Turning now to FIGS. 1-5B the details of the trackable trochar 20 will now be described, first by describing its various components and then by describing its use and operation. The trackable trochar 20 basically comprises three component assemblies, namely, a luer lock-sheath assembly 22 best seen in FIG. 3, a handle-stylet assembly 24 best seen in FIGS. 4, 4A and 4B, and a handle-EM sensor assembly 26 best seen in FIGS. 5, 5A and 5B. The handle-EM sensor assembly 26 is arranged to be reused, while the luer lock-sheath assembly 22 and the stylet-handle assembly 24 are each single-use disposable members. Since the handle-EM sensor assembly 26 is arranged for reuse, it will be provided with a sterile, single use cover 4 (shown by the phantom lines in FIGS. 1 and 5) during use, as will be described later.

Figure 3:
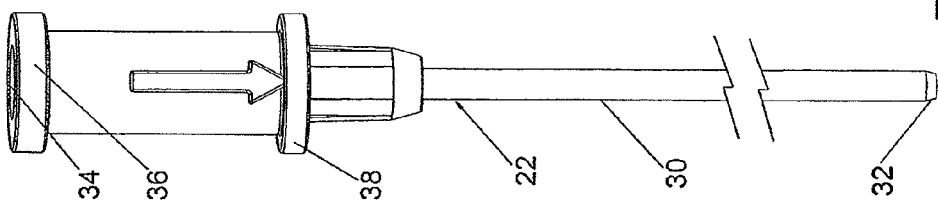
FIG. 3 is an enlarged isometric view of one component assembly of the trochar of FIG. 1, namely, an assembly of a luer connector and an associated tubular sheath.

The luer lock-sheath assembly 22 is best seen in FIG. 3 and basically comprises a conventional luer lock connector 28 and a conventional sheath or cannula 30 fixedly secured together. The sheath is an elongate linear tubular member that has an open distal end 32. The luer lock connector 28 is a hollow member whose proximal end is open at 34, i.e., is defined by a circular side wall 36. An annular ring 38 projects outward from the connector 28 to enable the user to readily grasp the luer lock-sheath assembly 22 during its use (to be described later). The luer lock-sheath assembly 22 is a disposable, i.e., single use, member adapted to be releasably mounted on the handle-stylet assembly 24. To that end, the circular sidewall 36 of the luer lock-sheath assembly 22 is arranged for disposition within an annular shaped recess in the handle-stylet assembly 24 to releasably frictionally secure those components together.

Figure 2:
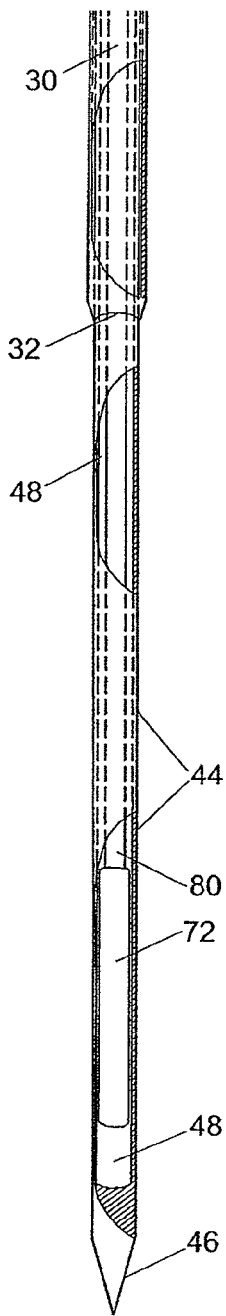
FIG. 2 is an enlarged side elevational view, partially in section, showing the distal end of the trochar shown in FIG. 1.
Figure 4:
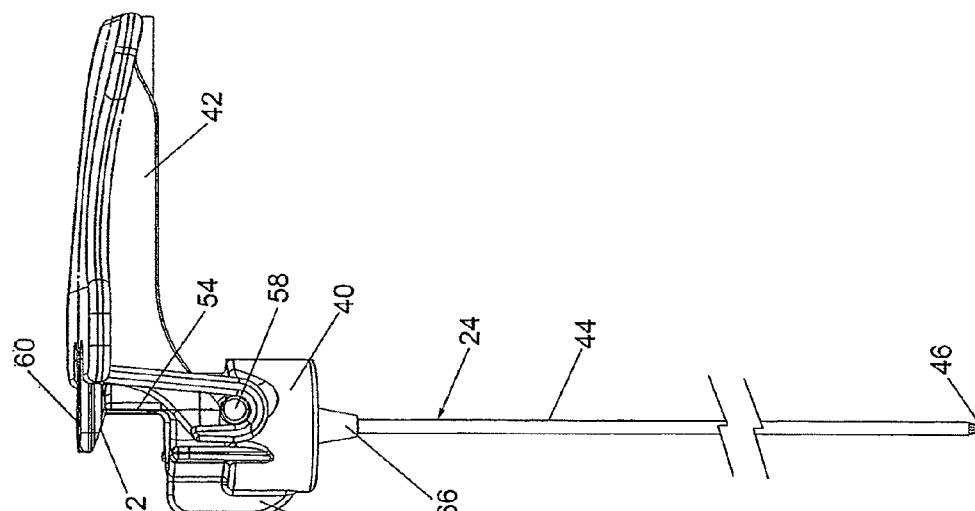
FIG. 4 is an is an enlarged isometric view of another component assembly of the trochar of FIG. 1, namely, an assembly of a handle and stylet.

The handle-stylet assembly 24 is best seen in FIG. 4 and basically comprises a hub 40, a pivotable handle 42 and a stylet 44. The stylet 44 is formed of any conventional material, e.g., stainless steel, and includes a sharpened or pointed distal tip 46. The stylet is hollow along most of its length, except for its distal end portion as shown in FIG. 2. The hollow interior of the stylet 44 forms a cavity 48 arranged for releasable receipt of an EM sensor and its associated cable forming a portion of the handle-EM sensor assembly 26. The stylet can be of any size, e.g., 16 gauge or smaller, for co-axial technique percutaneous tracking of its tip.

Figure 4A:
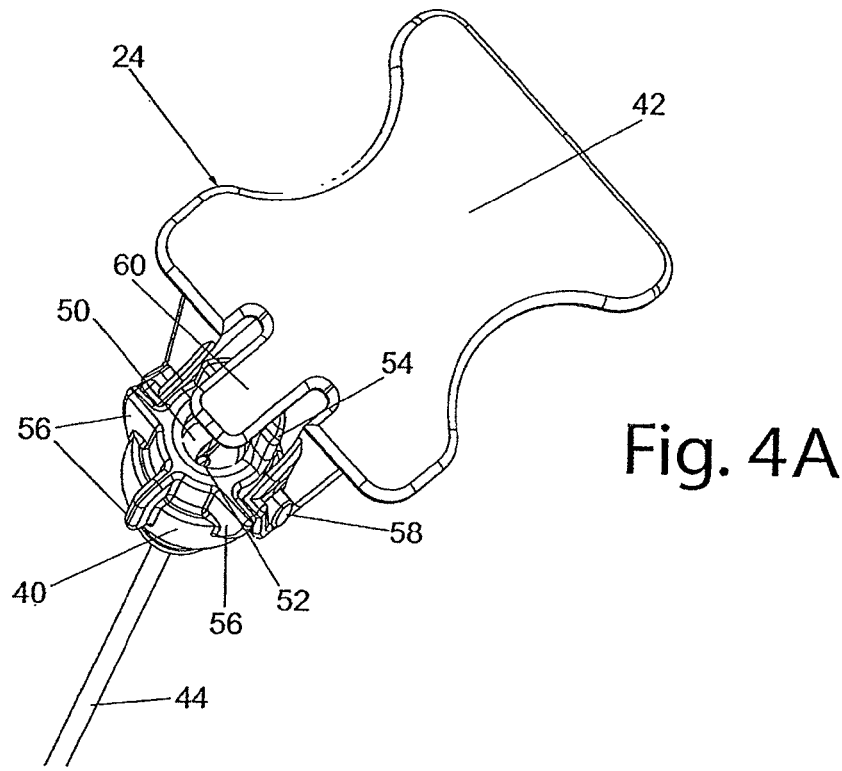
FIG. 4A is an enlarged isometric view of the handle shown in FIG. 4.
Figure 4B:
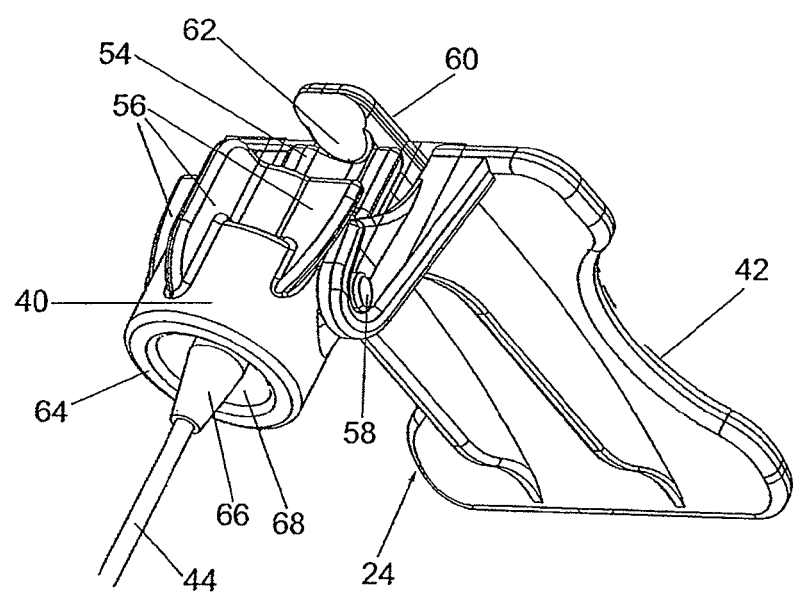
FIG. 4B is another enlarged isometric view of the handle shown in FIG. 4.

The hub 40 of the handle-stylet assembly 24 is best seen in FIGS. 4A and 4B and basically comprises a hollow member having a central recess 50 with an opening 52 at its nadir that is in communication with the cavity 48 in the stylet 44. An arcuate wall 54 projects upward from the hub 40. Three reinforcing ribs 56 project outward from the hub. The hub also includes a pair of pins 58 projecting diametrically outward from it perpendicular to the longitudinal axis of the hub. The pins serve to pivotably mount the handle 42 onto the hub. The top surface of the handle 42 is flat and includes a finger 60 having a sloped, e.g., 15 degree inclined, cam surface 62 on its underside. The finger 60 is somewhat flexible for reasons to become apparent later. A circular wall 64 projects downward from the hub 40. The point at which the stylet is connected to the hub 40 is in the form of a conically shaped projection 66. The circular wall 64 extends about the projection 66 to form an annular recess 68 into which the circular proximal portion of the wall 36 of the luer lock connector 28 is disposed to frictionally connect the luer lock-sheath assembly 22 to the handle-stylet assembly 24. When so connected the projection 66 of the handle-stylet assembly is located within the hollow interior of the luer lock connector 28 and the stylet 44 extends down the hollow interior of the sheath or cannula 30 and out its open end 32 (see FIG. 2).

The handle 42 of the handle-stylet assembly 24 is arranged to be selectively moved between a locked position, such as shown in FIGS. 1 and 4, to an unlocked position, and vice versa. When the handle 42 is in the locked position, as best seen in FIG. 4B, the undersurface 62 of the finger 60 overhangs the top surface of the upstanding wall 54, thereby releasably locking the handle in that position. When the handle is in the unlocked position, such as by rotating it in the clockwise direction, the finger 60 will be off of the upstanding wall 54, thereby fully exposing the hollow interior of the recess 50 in the hub. This action readies the handle-stylet assembly 24 to be coupled to the handle-EM sensor assembly 26, as will be described later.

Figure 5:
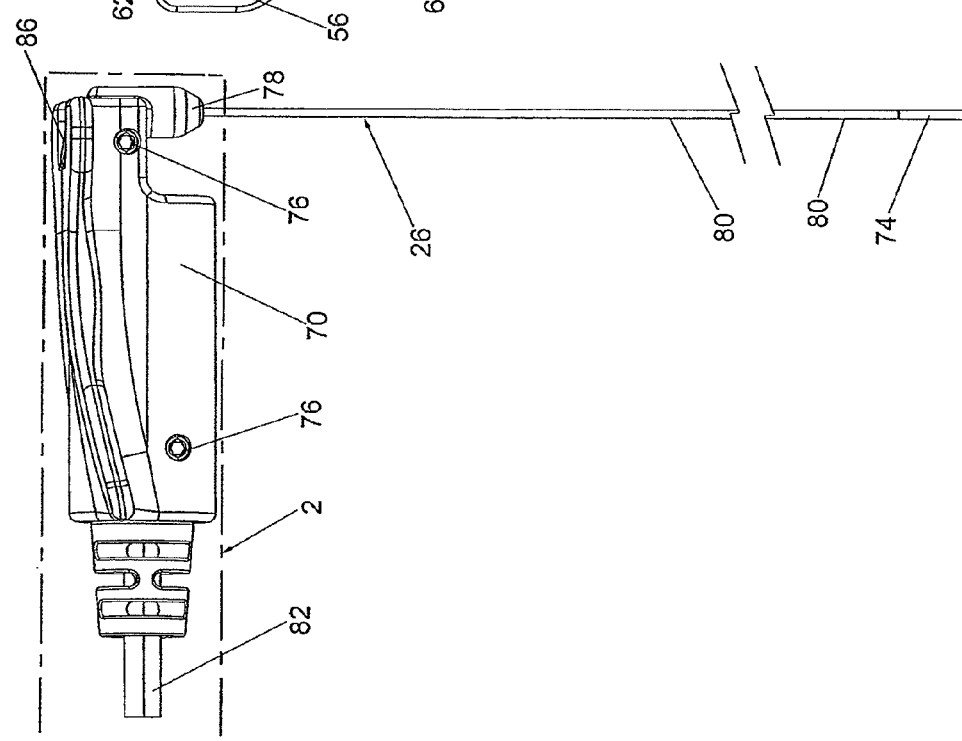
FIG. 5 is an is an enlarged isometric view of another component assembly of the trochar of FIG. 1, namely, an assembly of another or second handle, an EM sensor and its associated cable.
Figure 5A:
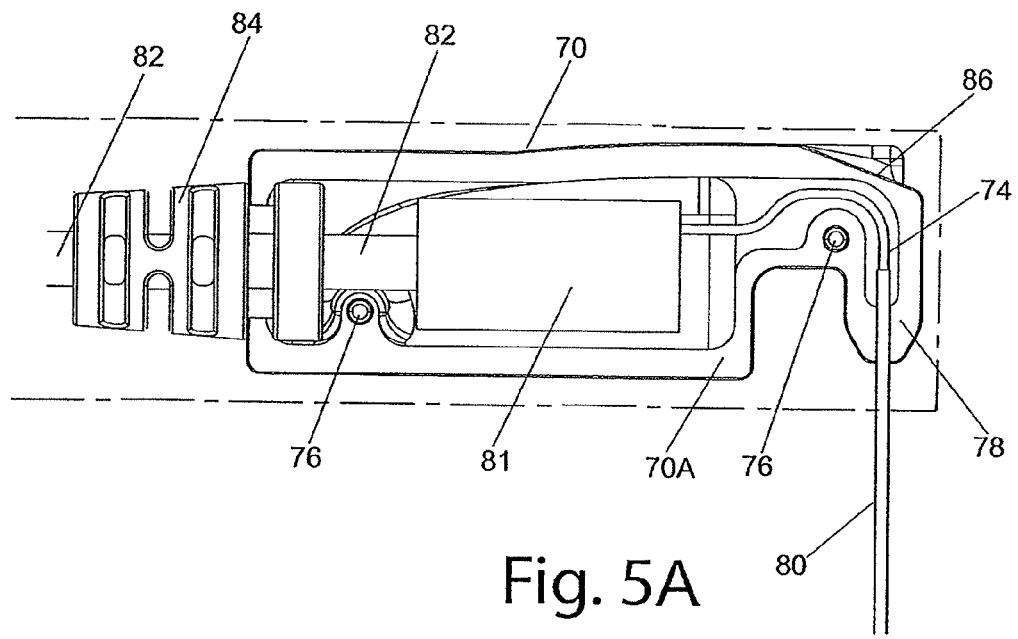
FIG. 5A is an enlarged isometric view of one of two sections of the handle shown in FIG. 5, with the other section of that handle removed.
Figure 5B:
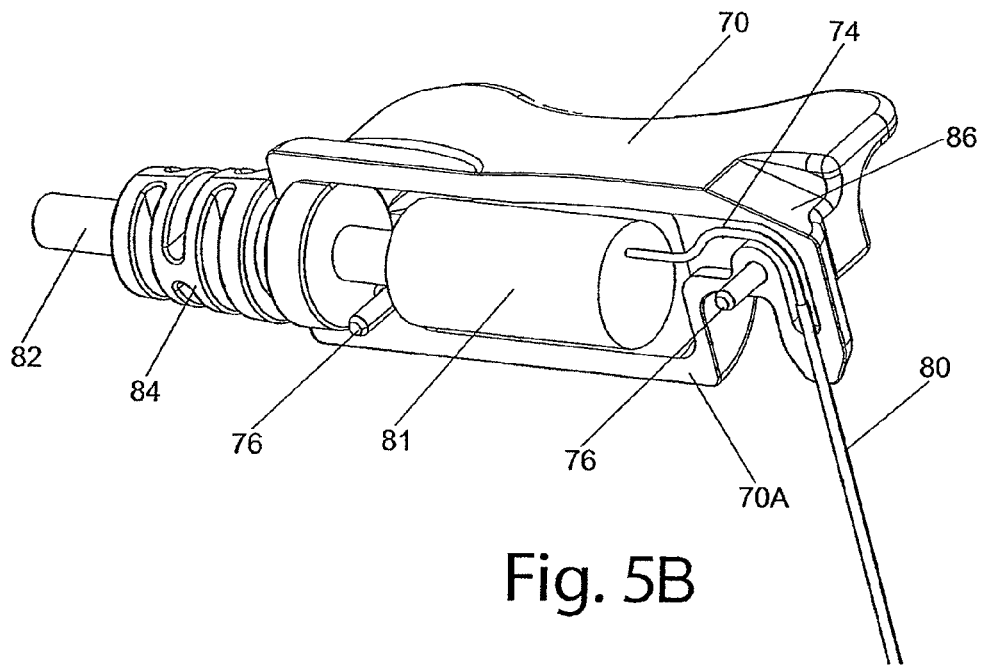
FIG. 5B is another enlarged isometric view of the section of the handle shown in FIG. 5A.

The handle-EM sensor assembly 26 is best seen in FIG. 5 and basically comprises a handle 70, an EM sensor 72 of conventional construction and an electrical cable 74 connected to the sensor 72. The handle 70 is composed of two hollow sections which are adapted to be secured together via a pair of screws 76. In FIGS. 5A and 5B only one handle section 70A is shown. The other section of the handle 70 is of identical construction to section 70A. As can be seen the handle 70 includes a downwardly projecting portion 78 through which a proximal portion of the sensor's cable 74 extends. The sensor cable 74 is a thin, relatively flexible member. In order to provide some rigidity or stiffness to the cable to facilitate its insertion and disposition and the sensor's insertion and disposition within the cavity 48 in the stylet a stiffening coating or tube 80 is provided along the entire length of the cable 74 from the sensor 72 up through the projection 78. Each of the handle sections making up handle 70 is hollow immediately to the rear of the projection 78. A cylindrical shield 81 is located within that hollow interior and serves to transition the proximal end of the small diameter sensor cable 74 into a larger and more robust cable section 82 which exits the handle 70 via a strain relief grommet 84. The top surface of the handle 70 is generally flat (like handle 42) and includes a downwardly canted cam surface 86 disposed immediately adjacent the projection 78. This surface is arranged to be pressed downward by the cam surface 62 on the undersurface of the finger 60 of the handle 42 of the handle-stylet assembly 24. This action causes the cover 2 which is disposed over the handle 70 to be tightly squeezed in the interface between the hub 40 of the handle-stylet assembly 24 and the projection 78 of the handle-sensor assembly 26, thereby isolating the sensor.

The assembly and use of the tracking trochar 20 will now be described. To that end, the handle 42 of the handle-stylet assembly 24 is pivoted in the clockwise direction to unlock it. In particular, the handle 42 is pushed downward to rotate it in the clockwise direction so that the undersurface 62 of the finger 60 flexes slightly and rides over the top surface of the upstanding wall 54 of the hub 40, thereby freeing the handle. Continued rotation of the handle in that direction will fully expose the hollow interior of the recess 50 in the hub 40. This enables a portion of the handle-EM sensor assembly 26 to be inserted therein so that the sensor can be disposed within the cavity in the stylet. Before doing that the cover 2 is disposed over the handle 70 of the handle-EM sensor assembly 26. The cover 2 is a flexible somewhat resilient member, shaped like a condom, and includes a small opening at one end thereof. The cover is disposed over the handle 70 with the cable extending through the opening. The opening in the cover is sized so that it fits tightly about the stiffening coating or tube 80 on the sensor cable 74. Once the cover 2 is in place on the handle-EM sensor assembly 26, that assembly is moved with respect to the handle-stylet assembly 24 so that the sensor 74 enters into the recess 50, through opening 52 and down through the central channel 48 in the stylet 44 until the sensor is located adjacent the closed distal end of the stylet, e.g., is in a position like shown in FIG. 2. Once that has occurred the handle 42 can then be rotated back in the counterclockwise direction, whereupon the finger 60 flexes somewhat and the cam surface 62 on the underside of the finger rides over the top edge of the upstanding wall 54 of the hub until it clears the inner surface thereof, whereupon the finger snaps downward to trap the wall, thereby releasably locking the handle 42 in the closed position. In this position the cam surface 62 engages a correspondingly shaped surface 86 on the handle 70 of the handle-EM sensor assembly 26, thereby pressing downward on that handle. This action presses the projection 78 deeper into the recess 50 of the hub of the handle-stylet assembly, thereby tightly sandwiching the cover 2 therebetween to effectively isolate the sensor from the ambient surroundings and releasably lock the two assemblies 24 and 26 together. The stylet of the connected assemblies 24 and 26 can now be inserted into the luer lock-sheath assembly 22. To that end, the distal end of the stylet 44 is inserted into the open proximal end 34 of the luer lock connector and down through the open end 32 of the sheath until the conically shaped projection 66 of the hub of the handle-stylet assembly 24 is fully within the hollow interior of the luer lock connector, i.e., the trackable trochar is in the configuration as shown in FIG. 1. At this point it is ready for use.

The EM sensor 72 enables the trackable trochar 20 to be tracked during its use, e.g., during any ultrasonically directed procedure, in a conventional manner by means of any suitable EM tracking system. For example, the trackable trochar 20 can be inserted percutaneously into any portion of the body of the patient while the EMT system is operated in conjunction with the ultrasound probe to monitor the trochar's position. Once in the desired position, the luer lock-sheath assembly 22 can be held in position by the user of the device while the handle-stylet assembly 24 and the handle-EM sensor assembly 26 are withdrawn as a unit, leaving the luer lock-sheath assembly 22 in place. Any elongated instrument (not shown) can then be introduced through the luer lock-sheath assembly 22 into the patient's body to accomplish the desired procedure, e.g., a biopsy procedure, an ablation procedure, a catheter placement, an intravascular procedure, and endoscopic procedure, etc.

The removed handle-stylet assembly 24 can then be disconnected from the handle-EM sensor assembly 26 and discarded. That disconnection is accomplished by pivoting the handle 42 of the handle-stylet assembly 24 in the clockwise direction to free the finger 60 from the upstanding wall 54 of the hub, as described above. The handle-EM sensor assembly 26 can then be moved with respect to the handle-stylet assembly 24 to withdraw the sensor 72 and its cable 74 from the interior of the stylet 44. The cover 2 can then be removed from the handle-EM sensor assembly, whereupon that assembly will be ready for reuse, i.e., introduction into the hollow interior of a new handle-stylet assembly after a new cover is placed on it.

As should be appreciated from the foregoing the trackable needle trochar 20 is arranged for insertion into the body of a patient via the sheath 30 for use in an image guided procedure on the patient, with the tip position of the instrument to be tracked with respect to the patient by an EMT system. This is critical because of the high likelihood of bending of the instrument during positioning proximal to the sensor. If this weren't the case then having the sensor attached further up the shaft would be equally accurate and satisfactory in all cases. The sensor is fixed to a handle at a chosen distance away via a reinforced/stiffened section of wires. The wires are of equal or smaller diameter than the sensor in most cases. This is of considerable importance as the diameter of the sensor becomes the limiting factor in how small a needle can be used to track the tip. Cabling is provided from the handle to a receiver plug that goes to a remote power supply and signal processing box (not shown). The strain relief manner at which cable exits the handle is provided in the interest of longevity. The handle-EM sensor assembly 26 is a pre-sterilized component that is intended for single use and includes a hollow needle tipped stylet with a handle and an overlying tubular sheath. Preferably, a sterile sleeve cover including a small hole in the center of the otherwise closed end will be included with this disposable stylet and sheath in a kit for the EM sensor portion. The overlying tubular sheath has a distal end and a proximal end at which a connector (e.g., a luer lock) is located. The distal end of the tubular sheath is open. The first member comprises a first handle and an elongated linear stylet secured to and projecting from the first handle. The linear stylet has a distal tip portion that is closed/sealed and a hollow interior cavity terminating adjacent the distal tip portion. In use, the EM sensor is disposed within the stylet cavity and located adjacent the distal tip portion of the stylet with the stiffened section of electrical cable extending along the length of and out of the stylet cavity into the second handle through which the sensor wires pass. The handle of the stylet and the handle of the sensor are adapted to be releasably locked together to form a T handle when combined and to provide a lateral exit for the sensor cable from the handle of the trochar. The sterile sleeve cover is designed with a small hole in the tip that is required to let the sensor and the stiffened section of wiring leading up to the handle to pass through the sleeve yet allow the sleeve to entirely cover the remaining portion of the reusable handle and cable. The locking section of the stylet handle is designed to compress the junction of the stylet handle and the sensor handle to create a watertight seal using the sterile plastic sleeve cover as the sealing gasket at the junction. The tubular sheath 30 is of a designed length such that when locked in position over the stylet the distal tip portion of the stylet extends out of the open end of the tubular sheath. Since the sensor, the stiffened section of sensor wire, the sensor handle and the associated cable are fully covered by the combination of the sealed tip stylet and the sterile sleeve during any procedure, and are removed from the cavity of the stylet and uncovered in a controlled manner only when the procedure is completed, it is possible to reuse the sensor repeatedly in sterile procedures without any need for cleaning or sterilization. The other components of the needle trochar assembly 20 are all single-use and disposed of at the end of a procedure.

Figure 6:
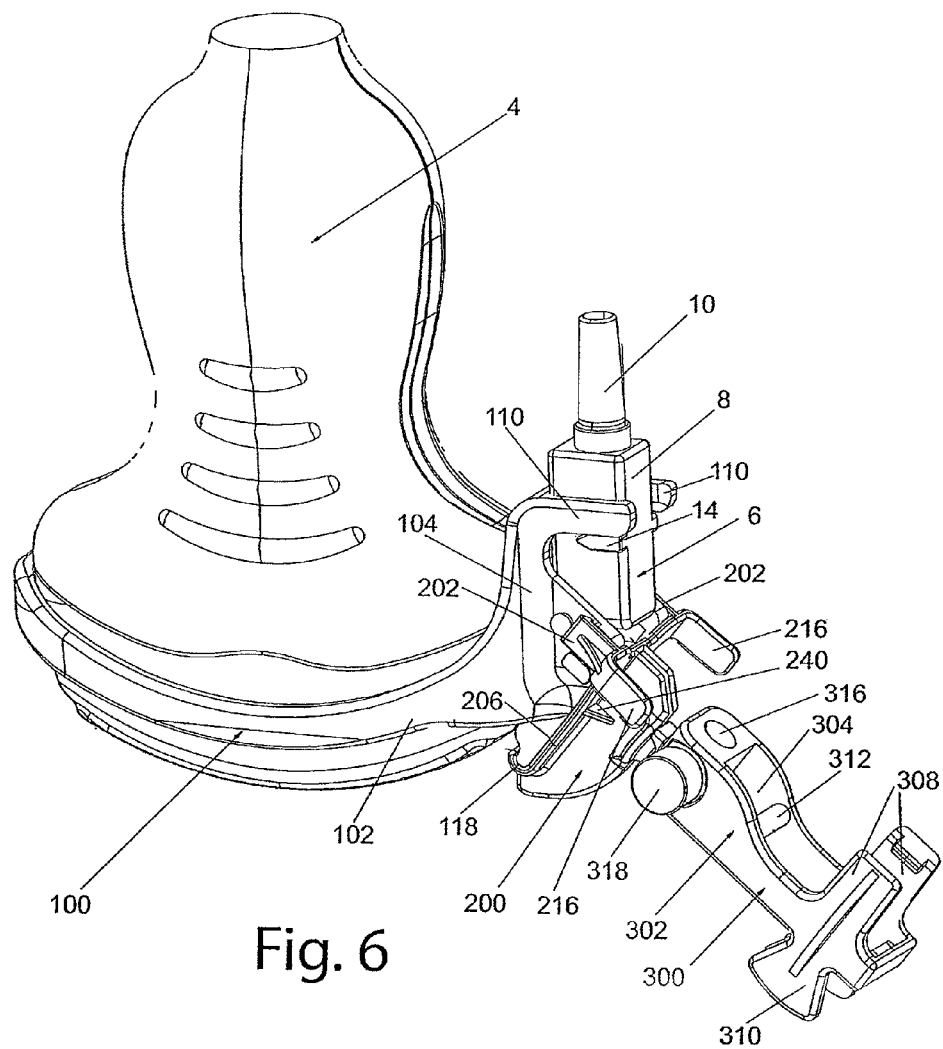
FIG. 6 is an isometric view of a conventional ultrasound transducer on which an EM sensor-mounted bracket is disposed, with a slotted needle guide mounted on the bracket and with an instrument adapter shown being registered to the needle guide, all of which form respective portions of the EMT system of this invention.

Referring now to FIG. 6 the details of the transducer bracket 100 and its associated components will now be described. To that end, as can be seen the bracket 100 is shown releasably mounted on a conventional ultrasonic transducer or probe 4. As is conventional a sterile cover (not shown) is interposed between the bracket and the transducer. The bracket 100 serves to releasably mount an EM sensor assembly 6 thereon. The sensor assembly 6 is a reusable component that comprises a conventional EM sensor disposed within a sealed housing 8. With the sensor assembly 6 disposed on the transducer 4, the transducer can be tracked with respect to some frame (not shown) or image set to fuse or register the live ultrasound image to a previously taken image, e.g., a CT scan. This enables the practitioner to navigate the patient's internal anatomy to a desired location with assurance. The sealed housing 8 is a small plastic member having an engineered shape that suits various purposes. The primary purpose is for releasably locking to various tools in the tool set. Another purpose is a keying feature (to be described later) for use in registration of the tools for checking for accuracy of position within the navigation field or for additional registration to images using the passive markers for example. The sensors placed within this housing may be larger and or less costly than the smaller sensors used for the needle trochar 20 with tip tracking described above. These are typically 6 DOF sensors and are precisely located within the housing. In addition, to assure accuracy, their position relative to the external surfaces/features of the housing is calibrated and adjusted electronically during production to a chosen, known and reproducible position. This enables the sensors to become a modular component from the standpoint of the software and other tools in the tool set so that they may be used with most of the tools in the tool set interchangeably.

The bracket 100 basically comprises a ring-like body member 102 which is arranged to snap-fit about a portion of the periphery of the probe 4, e.g., about the lower or distal portion of the probe as shown in FIG. 6. The bracket is preferably an integral member, e.g., a molded component formed of any suitable material, e.g., plastic. The ring-like body member 102 includes an upstanding portion 104 which forms a socket for releasably mounting the EM sensor assembly 6. The socket 104 is defined by a pair of spaced apart walls 106 which project outward and away from the ring-like body portion to form a cavity 108 for receipt of the sensor assembly 6. The upper end of each wall 106 is in the form of a projecting arm 110. A cylindrical pin 112 extends through the cavity 108 between the lower end portions of the walls 106. The pin serves as a pivot point about which the sensor assembly can rotate to releasably mount it to the bracket (as will be described shortly). Before doing that a brief discussion of the details of the construction of the EM sensor assembly 6 is in order. To that end, as best seen in FIG. 9, the sensor assembly 6 basically comprises a generally parallelepiped shaped housing 8 in which the EM sensor itself (the electrical component, e.g., the EM coils) is mounted. The cable 10 for the sensor exits the housing 8 at the proximal end thereof at a strain relief component. The strain relief component is of significant importance to longevity of the sensor when re-used in this tool set and application(s). The corner of the housing at the distal end (i.e., the end opposite from the cable egress end) includes a semi-circular shaped recess 12 extending across the width of the housing. The radius of the recess 12 is the same or just slightly larger than the radius of the pin 112.

The releasable mounting of the sensor assembly 6 to the bracket is accomplished by orienting it so that its body 8 is generally perpendicular to the upstanding body portion 104 of the bracket, with its semicircular recess 12 pointed towards and aligned with the pin 112 extending through the bracket's socket. The sensor assembly can then be mounted on the pin (i.e., the pin 112 received within the recess 12) and once that has been accomplished, the sensor housing can be rotated upward about the pin, whereupon the proximal end portion of the sensor housing snap-fits between the projecting arms 110. This action releasably locks the sensor assembly 6 in the socket of the bracket 100. In order to guide the sensor into this releasably locked position, the sensor housing 8 includes a pair of guide members 14 on opposite sides thereof. The inner end of each guide member is in the form of a sloped cam surface 16. As will be appreciated by those skilled in the art, when the sensor housing is rotated to lock it in place, the sloped surface of each guide will engage the undersurface of a respective one of the projecting arms 106 and ride thereover until the top (distal) surface of each guide member is in abutment with the undersurface of its respective projecting arm. When the sensor assembly is in this position it is effectively snap-fit or locked in the bracket's socket and is thus resistant from accidental disconnection. If and when it is desired to remove the sensor assembly from the bracket, all that is required is to rotate its proximal end downward, i.e., in the clockwise direction, so that it passes between the projecting arms 106. Once the sensor housing 8 is free of those arms the sensor assembly 6 can be removed from the pin in the socket.

Figure 7:
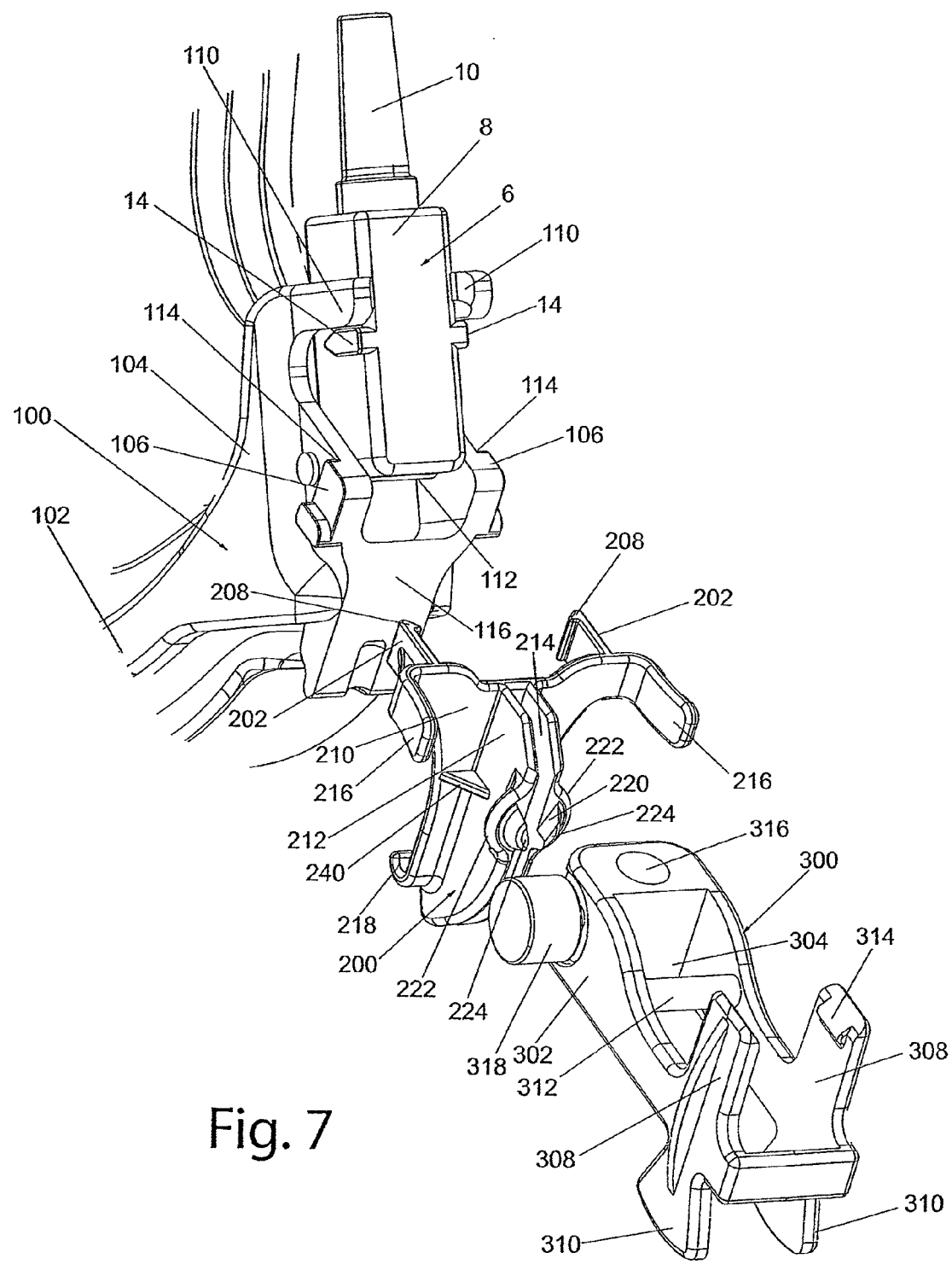
FIG. 7 is an exploded isometric view of the EMT system components shown in FIG. 6.

The bracket 100 also includes a portion for mounting the heretofore identified slotted needle guide 200 on it. In particular, the lower end portion of each wall 106 just below the pin 112 is thickened to form an undercut surface 114 (FIG. 7). The end surfaces of the bottom portion of each wall 106 are coplanar with a sloping, guide-receiving planar surface 116. The surface 116 is arranged to have an inner surface (to be described later) of the needle guide 200 juxtaposed to it when the needle guide is mounted on the bracket 100. The body portion 104 of the bracket also includes a pair of axially aligned semi-circular convex surfaces 118 immediately below the lower edge of the guide receiving surface 116. These convex surfaces serve as pivot points about which a portion of the slotted needle guide 200 can be rotated to releasably snap-fit the needle guide to the bracket. In the furtherance of the snap-fitting of the needle guide to the bracket the needle guide also includes a pair of projecting arms 202 (to be described later) that are arranged to snap-fit to respective ones of the undercut surfaces 114 of the bracket 100.

The details of the construction of the needle guide 200 will now be described with reference to FIGS. 6 and 7. The needle guide is preferably formed as an integral unit of any suitable material, e.g., a plastic, and basically comprises a generally T-shaped body member 204 having a generally planar front surface 206. That surface is the surface that is arranged to be juxtaposed to the receiving surface 116 of the bracket 100 when the needle guide is mounted on the bracket. The heretofore mentioned projecting arms 202 of the needle guide project outward from the top portion of the front surface 206 of the T-shaped body member and are spaced apart by a sufficient distance to accommodate the thickened lower portion of the two walls 106 of the bracket 100 therebetween. Each of the arms 202 terminates in a flanged tip 208 having a cam or sloped outer surface and an undercut lower surface. The body member 204 also includes a rear surface 210, from which a pair of walls 212 extend. The walls 212 form a channel 214 between them which is adapted to receive a needle or some other elongated instrument to serve as an orientation guide to facilitate in-plane instrument manipulations within the channel. A pair of squeeze tabs 216 project backward from the upper end of the T-shaped body member adjacent respective ones of the arms 208. The lower end the T-shaped body member at the front surface 206 is in the form of a pair of axially aligned concave recesses 218, each of which is arranged to receive a respective one of the axially aligned semi-circular convex surfaces 118 of the bracket 100 to mount the needle guide 200 on the bracket. That action is accomplished by positioning the needle guide 200 so that it is tilted slightly downward (i.e., rotated slightly in the clockwise direction) from the orientation shown in FIGS. 6 and 7. The needle guide is then brought into position so that its concave recesses 218 receive respective ones of the semi-circular convex surfaces 118 of the bracket. When that has been achieved, the needle guide 200 can be tilted upward, i.e., rotated in the counterclockwise direction, whereupon the cam surfaces on the tips of the arms 202 ride over the front surface of the thickened portions of the walls 106 of the bracket, until their undercut portions snap-fit into engagement with respective undercut portions 114 of those walls. This action effectively snap-fits or locks the needle guide 200 onto the transducer bracket 100 with sufficient strength to be resistant from accidental disconnection. In order to guide the needle guide 200 into this releasably locked position on the bracket 100, the bracket 100 includes a pair of guide members 14 on opposite sides thereof. The guide members 14 are like those on the housing 8 of the EM sensor assembly 6. To that end, the inner end of each guide member 14 on the bracket 100 is a sloped cam surface 16. Thus, when the needle guide 200 is rotated in the counterclockwise direction to lock it in place on the bracket 100, the sloped surface of each guide 14 member will engage the undersurface of a respective one of the projecting arms 202 and ride thereover until the top surface of each guide member is in abutment with the undersurface of its respective projecting arm. When the needle guide 200 is in this position it is effectively snap-fit or locked to the bracket and is thus resistant from accidental disconnection.

If and when it is desired to remove the needle guide 200 from the bracket 100, all that is required is for the user to grasp the two squeeze tabs 216 between his/her fingers and squeeze them together. This action has the effect of slightly flexing the opposed arms 202 apart from each other, thereby freeing the tips of those arms from the undercut surfaces 114 of the bracket 100. Once the tips of the arms 202 are free of the undercut surfaces 114 of the bracket, the needle guide 200 can be tilted downward (i.e., rotated in the clockwise direction) about the pivot axis formed by the engaging surfaces 118 and 218 until the arms 202 are free of the bracket.

As will be described in detail later the needle guide 200 also includes two keying components, 220 and 240, each of which is adapted to be coupled to corresponding keying components of other portions of the EM system of this invention.

Referring to FIGS. 8-11 the details of the EM sensor-equipped adapter device 300 will now be discussed. As mentioned earlier this component is arranged to be mounted on any conventional, e.g., disposable, needle 500, such as shown in FIGS. 13 and 14, or any other elongated linear medical instrument (e.g., any needle, rigid catheter, needle on a syringe (i.e., forming a guided syringe, rigid scope, etc.) used in an image guided procedure on a patient to convert that instrument into an EM trackable instrument. The device 300 can have different ergonomic geometries depending on the application. In general, the device 300 has a receiving feature (to be described later) for accommodating an EM sensor. The sensor is itself permanently fixed (disposed) within a special housing like that described above. The construction/shape of the device 300 allows the sensor in its housing and covered by a sterile sleeve barrier to be releasably secured to the linear instrument. Moreover, the receiving feature of the adapter device keeps the EM sensor and its housing in a fixed orientation to the linear instrument even when the sensor and its housing are covered with the sterile sleeve barrier. This allows a software calculation/determination of the location and orientation of the linear instrument in an EM field if length information is supplied once the device is fixed at a chosen point along the long axis of the instrument (as will be described later). The sleeve barrier allows re-use of the sensor without re-processing or sterilization. As will also be described later, the device 300 has a distal end portion with an adjustable cavity to accommodate and to lock to round, linear instruments of varied diameter (22 Gauge to 8 French). The adapter 300 is comprised of a frame that holds this attachment feature and a receiving feature for the EM sensor in its housing. The entire device/assembly is releasably securable to the linear instrument at various positions along the length of the instrument, but most typically will be located toward one end as far from the pointed tip as possible. In the exemplary embodiment described above it is made of injection molded plastic and is pre-sterilized for single use.

As can best be seen in FIGS. 8 and 9 the adapter 300 basically comprises a housing 302 having a cavity 304 (FIG. 9) shaped to accommodate an EM sensor assembly 6, like that described previously. The cavity 304 is formed between a pair of side walls 306. A pair of fingers 308 project upward from respective ones of the side walls 306 at the proximal end of the housing 302. A pair of squeeze tabs 310 projects downward from respective ones of the side walls 306 opposite to respective ones of the fingers 308. A pin 312 extends between the side walls 306 within the cavity 304. The pin 312 is constructed similarly to the pin 112 of the bracket 100 to enable the releasable pivotable mounting of the sensor assembly 6 in the cavity as will be described shortly. The free end of each of the fingers 308 includes an inwardly directed flange 314 forming a cam surface.

The distal end of the housing 302 is solid and includes a passageway or hole 316 extending fully through it. The hole is adapted to receive the elongated body of a conventional needle 500 (FIG. 13) or any other elongated medical device, e.g., catheter, scope, etc. In order to facilitate the placement of the adapter on the needle or other elongated instrument, the entry to the hole 316 is chamfered. A thumbscrew 318 is mounted on the distal end of the housing so that its free end is in communication with the interior of the hole 316. When a needle or other elongated instrument is extended through the adapter's hole 316, the adapter can be positioned at any longitudinal position along the needle/instrument. Once it is in the desired position, it can be releasably locked in that position by tightening of the thumbscrew 318, which action brings the free end of the thumbscrew into intimate engagement with the portion of the needle/instrument located within the hole.

The adapter 300 is relatively small, e.g., it takes up only approximately 1 cm of needle/instrument length, and can be mounted on or removed easily from a straight cylindrical instrument of a range of sizes (22 G to 8 French). The electrical cable of the sensor assembly 6 mounted in the housing 302 exits from the side of the housing, i.e., 90 degrees from longitudinal axis of the needle/instrument. This feature reduces the tendency for the sensor-equipped adapter to be accidentally displaced along the needle/instrument by pulling on the sensor's cable.

The adapter 300 is preferably a disposable, single-use component, but may be constructed so that it is reusable. The sensor assembly 6, however, being a relatively expensive component is a reusable. Thus, when used it must be isolated from the ambient surroundings. To that end a thin cover (not shown) shaped somewhat like a condom is placed over the housing 8 of the sensor assembly 6 before mounting it in the adapter 300. The covered sensor assembly can then be releasably mounted in the housing 302 of the adapter 300. In particular, the releasable mounting of the EM sensor assembly 6 in the housing 302 of the adapter 300 is accomplished by orienting the covered body 8 of the sensor assembly until it is generally perpendicular to the longitudinal axis of the adapter's housing 302, with the semicircular recess 12 at the distal end of the housing 8 being pointed towards and aligned with the pin 312 extending through the cavity 304. The sensor assembly 6 can then be mounted on the pin (i.e., the pin 112 received within the recess 312 with a portion of the cover interposed therebetween) and once that has been accomplished, the covered sensor housing can be tilted downward about the pin, e.g., rotated in the clockwise direction, whereupon the proximal end portion of the sensor housing snap-fits over the cam surfaces at the tips of the projecting arms 308 and then into position between those arms. The guide members 14 operate on the distal surfaces of the arms 308 in a similar manner as described above with respect to the mounting of the sensor assembly to the bracket 100. This action releasably locks (snap-fits) the covered sensor assembly in the adapter so that it is resistant from accidental disconnection as clearly shown in FIGS. 8, 10, 11 and 13.

If and when it is desired to remove the sensor assembly 6 from the adapter 300, all that is required is for the user to grasp the two squeeze tabs 310 between his/her fingers and squeeze them together. This action has the effect of slightly flexing the opposed arms 308 apart from each other, thereby freeing the tips of those arms from the sensor housing 8. Once the tips of the arms are free of the housing, the sensor assembly with its cover can be rotated about the pin 312 until it can be fully removed from the cavity of the adapter. The cover can then be disposed of and the sensor assembly readied for reuse with another adapter 300 or some other component of this system.

As should be appreciated by those skilled in the art with an EM sensor assembly mounted in the adapter 300 and the adapter mounted on a needle 500 or any other elongated instrument, the needle/instrument is effectively transformed into a device that can be readily tracked by any EM tracking system. Moreover, the adapter 300 is arranged to be registered to the transducer, which itself is registered in the EM tracking system (e.g., via the EM sensor in the bracket 100).

The registration of the adapter 300 to the transducer is accomplished by means of a keying element. That element basically comprises a generally triangular shaped member 320 projecting outward from the distal surface of the adapter's housing 302. The keying element 320 is adapted to cooperate with a correspondingly shaped keying element on the needle guide 200 mounted on the transducer 4 via the bracket 100. The keying element on the needle guide for achieving that end is the heretofore identified element 220. The details of that element will now be described with reference to FIG. 7. In particular, as can be seen the free edge of each of the walls 212 forming the channel 214 of the needle guide includes a semi-circular flange 222 extending outward in the plane of the free edge. Each flange includes a projection 224 located thereon. Each projection 224 includes a conical surface forming a portion of its periphery and an angled side surface forming another portion of the periphery of the projection. The angled side surfaces of the two projections together define a V-shaped notch between them. The V-shaped notch forms the heretofore identified keying element 220. In particular, the triangular projection 320 of the adapter 300 is adapted to be inserted into the V-shaped notch 220 of the needle guide 200. With the adapter being mounted on a needle 500, like shown in FIG. 13, the needle can be registered to the transducer in the EM system by merely orienting the adapter so that its keying element 320 is disposed within the V-shaped notch 220 of a needle guide 200 that is itself mounted on a transducer 4 via a bracket, like bracket 100. Thus, the EMT system can be provided with information as to the position and orientation of the needle 500.

The conical peripheral portions of the two projections 224 that are located on the flanges 222 together form a projecting member that serves as another keying element of this invention. In particular, that other keying element can be used to register other components of the EMT system, e.g., the adhesive marker 400, as will be described later.

As should be appreciated from the foregoing, the sensor-equipped adapter 300 is suitable to convert any conventional off-the-shelf instrument into an EM guided instrument with high accuracy as long as the instrument doesn't bend. If the needle or other instrument is bendable, so that the location of the tip may not be where expected due to the needle's bending within the body of the patient, the EMT system should be able to register or track the needle's tip. The subject invention achieves that end by providing a keying element that enables the system to register the needle's tip with respect to the sensor-equipped adapter. This is particularly important since the adapter 300 can be positioned at any longitudinal position along the needle. That keying element basically comprises a gusset 240 which is located at the interface of the wall 212 and the rear surface 210 of the needle guide. Accordingly, after the needle 500 having the sensor-equipped adapter 300 mounted thereon has been registered to the EM system by placing the adapter's keying element 320 into the corresponding keying element 220 of the needle guide 200, as described above, the tip of the needle can be registered to the EMT system. That is accomplished by removing the needle 500/adapter 300 combination from the needle guide 200 and orienting the needle/adapter combination like shown in FIG. 14, so that the tip of the needle rests on the gusset 240 while the contiguous portion of the needle extends along the interface of the wall 212 and the surface 210. The EMT system can then determine the distance between the sensor and the tip of the needle using the information as to where the sensor of the assembly 6 in the adapter 300 is now located and oriented and the information previously stored in the system when the needle/adapter was initially registered to the transducer.

It should be pointed out at this juncture that it is expected that the registering of the location and orientation of the transducer 4 with respect to the anatomy of the patient in an ultrasound procedure will be accomplished by use of the sensor assembly 6 mounted in the bracket 100. However, it is contemplated that such registration can also be accomplished by using a sensor-equipped adapter 300 and coupling that adapter to a needle guide mounted on the transducer via a bracket 100.

As mentioned above the EMT system of this invention also includes a skin marker 400. That marker is a conventional device, e.g., a passive marker, which has been modified to include a keying element 402 to enable it to be registered into an EMT system using several of the components of this invention. To that end, the skin marker 400 comprises a disk-like body 404 having an adhesive undersurface and a central hub 406 including a top surface in which a conically shaped recess is centrally located. The bottom surface of the conically shaped recess can be flat or conical. In any case, the recess forms the keying element 402.

The sensor-equipped adapter 300 can be used to register the marker 400 into the EMT system after the marker has been positioned on the patient's body and imaged. To that end, the adapter housing 302 includes a complementary shaped and sized conical projection 322 on its side wall located generally opposite to the thumbscrew 318. Thus, to register the passive marker 400, all that is required is to take a sensor-equipped adapter 300 over to the passive marker so that the keying projection 322 of the marker is located within the keying recess 402. The EMT system can then be operated to register the location of the marker. Once that has been accomplished the sensor-equipped adapter 300 can be removed.

The marker 400 can also be registered into the EMT system by means other than an EM sensor equipped adapter 300. For example, the marker can be registered by the EM sensor mounted on the transducer bracket 100 via the use of the needle guide 200. In particular, a transducer having a sensor-equipped bracket 100 on which a needle guide 200 is mounted, like shown in FIG. 6, can be used to register the marker. Such action is accomplished by manipulating the transducer with the bracket/needle guide mounted thereon into an orientation such that the conical projection made up of the two flanged projections 224 of the needle guide 200 (i.e., the needle guide's "other keying element") fits within keying recess 402 of the marker. Once so positioned the EMT system can be used to record the location of the sensor mounted on the bracket to thus register the location of the marker 400.

The marker 400 can also be registered into the EMT system by the trackable trochar 20. For such applications it is preferable that the bottom of the keying recess 402 should have a central depression to accept the pointed tip 46 of the stylet 44. That central depression may be formed by another conical surface. Thus, to register the marker with the tracking trochar 20, all that is required is to insert the tip of the stylet into the recess 402 so that the tip 46 is at the nadir of that recess and then operate the EMT system to take a reading of the location of the sensor, and hence of the marker.

The EM sensor in its housing can be used interchangeably with the tool 300 and also, with the active markers, with an ultrasound transducer. To that end, a first keying member on the sensor housing is arranged so that it may (if the software is not set up to do this automatically) be releasably coupled to the ultrasound transducer for system checks. The keying member on the sensor housing may be used to calibrate or check the calibration of the system (if the software supports this), alternatively the receptacle for the key may be located elsewhere e.g., to a slotted needle guide mounted on a bracket that is mounted on the ultrasound transducer, to enable the EMT system to register the sensor with respect to the ultrasound transducer. A second keying member may be provided on the ultrasound transducer, e.g., on the needle guide, so that the distal end portion of the instrument can be releasably coupled to the second keying member to enable the EMT system to register the (length) distal end portion of the instrument with respect to the sensor when using the linear instrument device described above. Alternatively, the software may allow the user to enter this length data manually.

As should be appreciated from the foregoing the system of this invention has wide applicability in that it enables registration of the sensor-equipped adapter, definition of the virtual needle position and length for the ultrasound tracking software, and confirmation of registration of the trackable trochar.

Without further elaboration the foregoing will so fully illustrate our invention that others may, by applying current or future knowledge, adopt the same for use under various conditions of service.

We claim:

1. A device for releasable mounting on an elongated, linear medical instrument, used in an ultrasound-guided procedure on a patient, the procedure being carried out by an ultrasound transducer to enable the position of the instrument to be tracked with respect to a patient by an EMT system, said device comprising a housing and an EM sensor, said housing being arranged to be releasably mounted on a first member that is coupled to the ultrasound transducer, the first member including a first keying element, said housing releasably mounting said sensor directly thereon and being directly releasably securable to the instrument at various positions along the length of the instrument, said housing comprising a first keying element, one of the first keying element of the first member and said first keying element of said housing being arranged to be releasably received within the other of the first keying element of the first member and said first keying element of said housing to enable the EMT system to register said sensor with respect to the ultrasound transducer.

2. The device of claim 1 wherein said housing is arranged to releasably frictionally engage the instrument at various positions along the length of the instrument.

3. The device of claim 1 wherein said first member comprises a bracket.

4. The device of claim 3 wherein the elongated linear instrument includes a distal end portion and wherein the bracket includes a second keying element, the second keying element being arranged to receive the distal end portion of the instrument to enable the EMT system to register the distal end of the instrument with respect to said sensor.

5. The device of claim 1 wherein said first member comprises a needle guide.

6. The device of claim 5 wherein the elongated linear instrument includes a distal end portion and wherein the needle guide includes a second keying element, the second keying element being arranged to receive the distal end portion of the instrument to enable the EMT system to register the distal end of the instrument with respect to said sensor.

7. The device of claim 1 wherein the EMT system includes a passive marker adapted to be releasably secured to the skin of the patient, said passive marker including a keying element, said keying element of said housing being arranged to mate with the keying element of the marker.

8. A device for use with an ultrasound transducer to releasably mount a sensor of a location sensing system on the transducer, the sensor having a body including an opposed pair of wall portions, said device comprising a member arranged to be releasably mounted on the transducer and including a cavity therein, said cavity having a pair of spaced-apart side walls, said device and the sensor being arranged to be releasably coupled together via a concave recess and a mating shaped convex surface to enable the sensor to be oriented in a first position for insertion between said spaced-apart side walls of said cavity to introduce said convex surface into said concave recess to enable the sensor to be rotated about the interface of said convex surface and said concave recess to a second position within said cavity, whereupon portions of said spaced-apart side walls of said cavity directly releasably engage respective wall portions of the sensor to deter accidental displacement of the sensor with respect to the transducer.

9. The device of claim 8 wherein said convex surface forms a portion of said device and wherein the recess forms a portion of the sensor.

10. The device of claim 9 wherein the sensor comprises an elongated body having a longitudinal axis, and wherein the recess is located in a lower portion of the body of the sensor and extends perpendicular to the longitudinal axis and wherein said convex surface of said device is elongated and extends along an axis extending generally perpendicular to said spaced-apart side walls.

11. The device of claim 10 wherein said cavity includes a longitudinal axis and wherein the longitudinal axis of the sensor is oriented parallel to said longitudinal axis of said cavity when the sensor is in the second position.

12. The device of claim 11 wherein the longitudinal axis of the sensor is oriented at an acute angle to said longitudinal axis of said cavity when the sensor is in said first position.

13. The device of claim 8 wherein the sensor includes a pair of guide members, and wherein each of said guide members is arranged to be engaged by a respective portion of a respective one of said spaced apart side walls when the sensor is in said second position.

14. The device of claim 13 wherein said portions of said spaced-apart side walls snap fit about portions of the sensor.

15. The device of claim 8 wherein said portions of said spaced-apart side walls snap fit about portions of the sensor.

16. In combination a sensor of a location sensing system and a device for use with an ultrasound transducer to releasably mount said sensor on the transducer, said sensor having a body including an opposed pair of wall portions, said device comprising a member arranged to be releasably mounted on the transducer and including a cavity therein, said cavity having a pair of spaced-apart side walls, said device and said sensor being arranged to be releasably coupled together via a concave recess and a mating shaped convex surface to enable said sensor to be oriented in a first position for insertion between said spaced-apart side walls of said cavity to introduce said convex surface into said concave recess to enable said sensor to be rotated about the interface of said convex surface and said concave recess to a second position within said cavity, whereupon portions of said spaced-apart side walls of said cavity directly releasably engage respective wall portions of said sensor to deter accidental displacement of said sensor with respect to the transducer.

17. The combination of claim 16 wherein said convex surface forms a portion of said device and wherein said recess forms a portion of said sensor.

18. The combination of claim 17 wherein said sensor comprises an elongated body having a longitudinal axis, and wherein said recess is located in a lower portion of said body and extends perpendicular to said longitudinal axis and wherein said convex surface of said device is elongated and extends along an axis extending generally perpendicular to said spaced-apart side walls.

19. The combination of claim 18 wherein said cavity includes a longitudinal axis and wherein said longitudinal axis of the sensor is oriented parallel to said longitudinal axis of said cavity when said sensor is in said second position.

20. The combination of claim 19 wherein said longitudinal axis of said sensor is oriented at an acute angle to said longitudinal axis of said cavity when said sensor is in said first position.

21. The combination of claim 16 wherein said sensor includes a pair of guide members, and wherein each of said guide members is arranged to be engaged by a respective portion of a respective one of said spaced apart side walls when said sensor is in said second position.

22. The combination of claim 21 wherein said portions of said spaced-apart side walls snap fit about portions of said sensor.

23. The combination of claim 16 wherein said portions of said spaced-apart side walls snap fit about portions of said sensor.

* * * * *